(12) United States Patent
Ting et al.

(10) Patent No.: US 6,207,773 B1
(45) Date of Patent: Mar. 27, 2001

(54) METALLOCENE CATALYST FOR PREPARING OLEFIN POLYMER

(75) Inventors: Ching Ting, Hsinchu; Jing-Cherng Tsai, Kaohsiung; Yi-Chun Chen, Hsinchu; Sung-Song Hua, Taipei Hsien; Tsai-Tien Su; Yu-Shan Chao, both of Hsinchu, all of (TW)

(73) Assignees: Industrial Technology Research Institute, Hsinchu; Taiwan Synthetic Rubber Corporation; Chinese Petroleum Corporation, both of Taipei, all of (TW)

( * ) Notice: Subject to any disclaimer, the term of this patent is extended or adjusted under 35 U.S.C. 154(b) by 0 days.

(21) Appl. No.: 09/362,024

(22) Filed: Jul. 28, 1999

(51) Int. Cl.⁷ ................ C08F 4/44; B01J 31/38
(52) U.S. Cl. .......... 526/127; 526/161; 526/943; 526/348.6; 526/348; 526/336; 526/281; 526/905; 526/916; 502/103; 502/117; 502/152; 556/11; 556/12; 556/53

(58) Field of Search .................. 556/11, 12, 53; 502/152, 103, 117; 526/127, 160, 943, 161, 348, 348.6, 916, 905, 336, 281

(56) References Cited

U.S. PATENT DOCUMENTS 5,892,079 * 4/1999 Wilson, Jr. .............. 556/11

* cited by examiner

*Primary Examiner*—David W. Wu
*Assistant Examiner*—R. Harlan
(74) *Attorney, Agent, or Firm*—Sughrue, Mion, Zinn, Macpeak & Seas, PLLC

(57) ABSTRACT

A metallocene complex in which the cyclopentadienyl group is substituted with an alkanediyl silyl group. The yield of the metallocene complex is high, and it can be used as the catalyst for preparing high molecular weight olefin polymers.

58 Claims, 2 Drawing Sheets

METALLOCENE CATALYST FOR PREPARING OLEFIN POLYMER

BACKGROUND OF THE INVENTION

1. Field of the Invention

The present invention relates to a novel metallocene complex, and more particularly to a novel metallocene complex in which the cyclopentadienyl group is substituted with an alkanediyl silyl group. Such a metallocene complex is suitable for preparing olefin polymers.

2. Background of the Invention

Olefin-based polymers have been used in a wide range of applications. One group of commonly used olefin-based polymers is polyolefins, that is, homopolymers or copolymers of olefins. These polyolefin plastics are typically used in such applications such as blow and injection molding, extrusion coating, film and sheeting, pipe, wire and cable.

An example of a polyolefin is ethylene-propylene elastomer (ethylene-propylene rubbers, EPR). It has many end-use applications due to its resistance to weather, good heat aging properties and its ability to be compounded with large quantities of fillers and plasticizers. Typical automotive uses are radiator and heater hoses, vacuum tubing, weather stripping and sponge doorseals. Typical industrial uses are sponge parts, gaskets and seals.

Another group of commonly used olefin-based polymers is terpolymers of ethylene, propylene, and a non-conjugated diene, which are generally referred to as EPDM elastomers. EPDM elastomers have outstanding weather and acid resistance, and high and low temperature performance properties. Such properties particularly suit EPDM elastomers for use in hoses, gaskets, belts, bumpers, as blending components for plastics and for tire side walls in the automotive industry; and for roofing applications. Additionally, because of their electrical insulation properties, EPDMs are particularly well suited for use as wire and cable insulation.

To date, many catalyst systems have been developed for olefin polymerization, these mainly being classified into two types: Ziegler-Natta catalyst systems and metallocene catalyst systems.

Ziegler et. al. in U.S. Pat. No. 3,113,115 uses $TiCl_4/AlEtCl_2$ catalyst system to produce EPR. Natta et. al. in U.S. Pat. No. 3,300,459 uses $VOCl_3/Al(C_6H_{13})_3$ catalyst system to produce EPR.

Floyd and Hoel in U.S. Pat. Nos. 5,001,205; 4,871,705; and 5,229,478 use metallocenes such as biscyclopentadienyl compounds to produce olefin polymers. The Dow Chemical Company in WO 9,308,221 and European Patent No. 0,416,815 A2 developed monocyclopentadienyl compounds, in which the cyclopentadienyl group is substituted with a constrain-inducing moiety, such as dimethylsilyl. However, synthesis of this particular constrained geometry catalyst (CGC) has a low yield, about 30%.

A need still exists for discovering a metallocene complex with a better yield that can be used as a catalyst in olefin polymerization.

SUMMARY OF THE INVENTION

The object of the present invention is to provide a metallocene complex with a high yield of up to 80%.

Another object of the present invention is to provide a metallocene complex capable of producing a high molecular weight olefin polymer with high catalytic activity.

To achieve the above-mentioned object, a metallocene complex is developed in the present invention which is represented by the following formula (I)

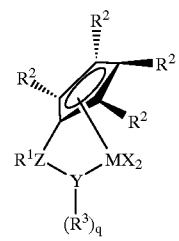

(I)

wherein:
M is a Group IVB transition metal with an oxidation state of +4;
Z is a Group IVA element;
$R^1$ is a divalent unsubstituted or substituted $C_{3-6}$ alkanediyl group which forms a ring system with Z, wherein the substituent is selected from the group consisting of $C_{1-20}$ alkyl, $C_{1-20}$ alkenyl, $C_{6-20}$ aryl, $C_{7-20}$ alkylaryl, and $C_{1-20}$ arylalkyl;
$R^2$ can be the same or different and is H, a $C_{1-20}$ linear, branched or cyclic hydrocarbyl. group, or a silyl group, or two adjacent $R^2$ groups combine together to form with the carbon atoms to which they are attached a $C_{4-6}$ fused ring system;
X is independently an anionic ligand with a −1 valence;
Y is a Group VA element or a Group VIA element;
q is 1 when Y is a Group VA element, and q is 0 when Y is a Group VIA element; and
$R^3$ is H, or a $C_{1-20}$ linear, branched or cyclic hydrocarbyl group.

The present invention provides another novel metallocene complex which is represented by the following formula (II):

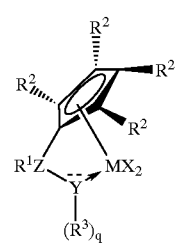

(II)

wherein:
M is selected from the group consisting of a Group IIIB transition metal, a lanthanide, and Ti with an oxidation state of +3;
Z is a Group IVA element;
$R^1$ is a divalent unsubstituted or substituted $C_{3-6}$ alkanediyl group which forms a ring system with Z, wherein the substituent is selected from the group consisting of $C_{1-20}$ alkyl, $C_{1-20}$ alkenyl, $C_{6-20}$ aryl, $C_{7-20}$ alkylaryl, and $C_{7-20}$ arylalkyl;
$R^2$ can be the same or different and is H, a $C_{1-20}$ linear, branched or cyclic hydrocarbyl group, or a silyl group, or two adjacent $R^2$ groups combine together to form with the carbon atoms to which they are attached a $C_{4-6}$ fused ring system;

X is independently an anionic ligand with a −1 valence;

Y is a Group VA element or a Group VIA element;

q is 2 when Y is a Group VA element, and q is 1 when Y is a Group VIA element; and $R^3$ is H, or a $C_{1-20}$ linear, branched or cyclic hydrocarbyl group.

DETAILED DESCRIPTION OF THE INVENTION

Figure 1:
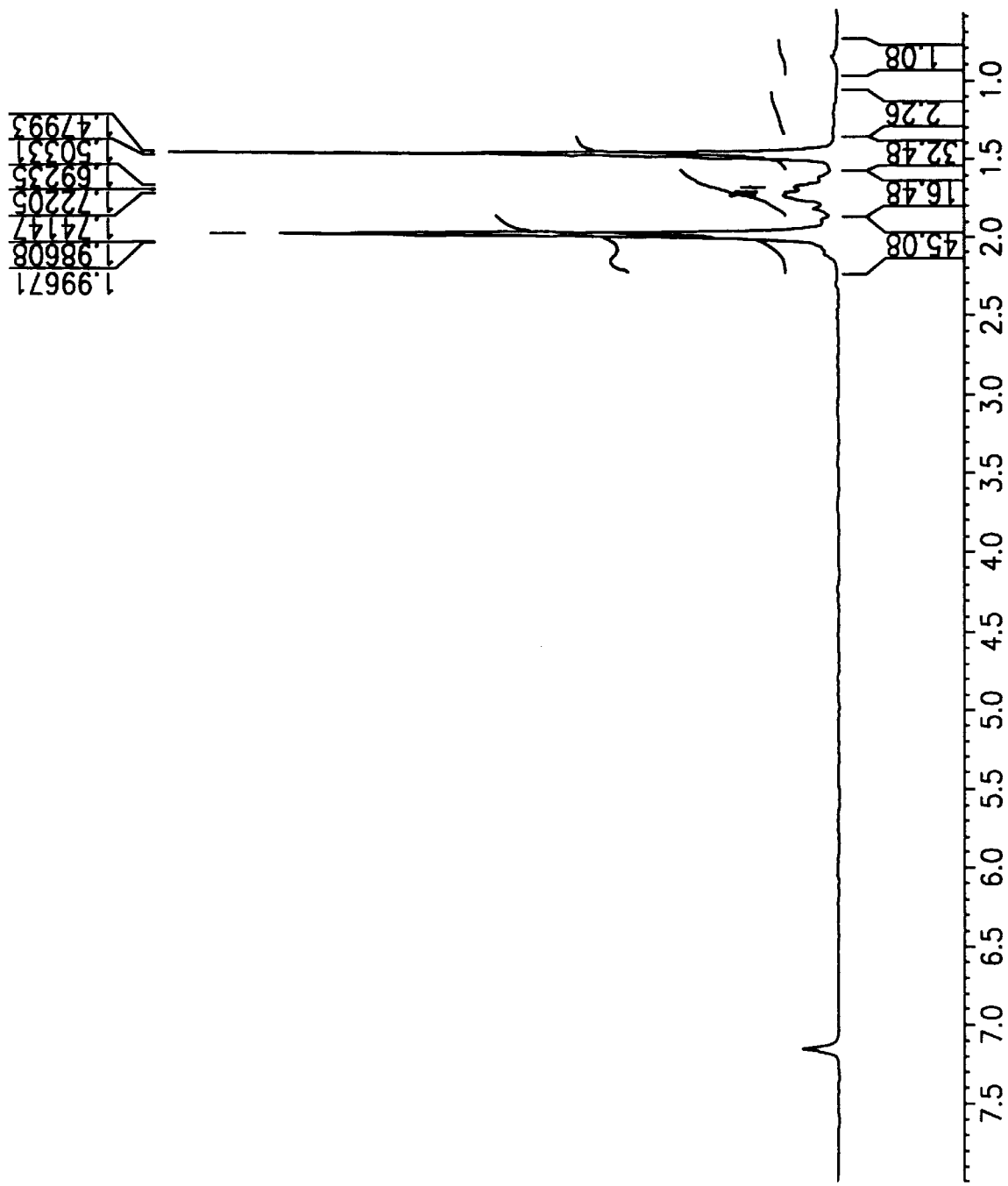
FIG. 1 shows the $^1$H NMR spectrum of a metallocene complex of the present invention.

The present invention provides two similar metallocene complexes, i.e., complexes of the formulae (I) and (II).

In formula (I), M is a Group IVB transition metal with an oxidation state of +4, such as titanium(+4), zirconium(+4), and hafnium(+4). Z is a Group IVA element, such as carbon, silicon, and germanium. $R^1$ can be a divalent unsubstituted or substituted $C_{3-6}$ alkanediyl group. The substituent can be $C_{1-20}$ alkyl, $C_{1-20}$ alkenyl, $C_{6-20}$ aryl, $C_{7-20}$ alkylaryl, or $C_{7-20}$ arylalkyl. Preferably, $R^1$ is a divalent unsubstituted $C_{3-6}$ alkanediyl group which forms a ring system with Z. Representative examples of $R^1$ include trimethylene, tetramethylene, pentamethylene, and hexamethylene.

$R^2$ can be the same or different and is independently H, a $C_{1-20}$ linear, branched or cyclic hydrocarbyl group, or a silyl group. The silyl group can be an alkyl silyl, a dialkyl silyl, a trialkyl silyl, a cycloalkyl silyl. Representative examples include methyl silyl, dimethyl silyl, trimethyl silyl, and methyl ethyl silyl. Alternatively, two adjacent $R^2$ groups can combine together to form with the carbon atoms to which they are attached a $C_{4-6}$ fused ring system.

Specifically, the $C_{1-20}$ linear, branched or cyclic hydrocarbyl group can be $C_{1-20}$ alkyl, $C_{1-20}$ alkenyl, $C_{6-20}$ aryl, $C_{7-20}$ alkylaryl, or $C_{7-20}$ arylalkyl. Representative examples of $R^2$ include H, methyl, ethyl, propyl, butyl, isobutyl, amyl, isoamyl, hexyl, 2-ethylhexyl, heptyl, octyl, vinyl, allyl, isopropenyl, phenyl, and tolyl.

Specifically, when two adjacent $R^2$ groups are combined together to form with the carbon atoms to which they are attached a $C_{4-6}$ fused ring system, $R^2$ can form with the cyclopentadienyl moiety on which they are attached to give a saturated or unsaturated polycyclic cyclopentadienyl ligand such as an indenyl, tetrahydroindenyl, fluorenyl or octahydrofluorenyl group.

Representative examples of $C_5(R^2)_4$ include $\eta^5$-cyclopentadienyl, $\eta^5$-methylcyclopentadienyl, $\eta^5$-ethylcyclopentadienyl, $\eta^5$-tetramethylcyclopentadienyl, $\eta^5$-pentamethylcyclopentadienyl, $\eta^5$-n-butylcyclopentadienyl, indenyl, tetrahydroindenyl, fluorenyl, and octahydrofluorenyl.

$R^3$ can be H, $C_{1-20}$ alkyl, $C_{1-20}$ alkenyl, $C_{6-20}$ aryl, $C_{7-20}$ alkylaryl, and $C_{1-20}$ arylalkyl.

Suitable examples of Group VA elements for Y are nitrogen, phosphorus, and arsenic, and suitable examples of Group VIA elements for Y are oxygen, sulfur, and selenium.

q is 1 when Y is a Group VA element, and q is 0 when Y is a Group VIA element. Representative examples of $Y(R^3)_q$ include —NH—, —N(CH$_3$)—, —N(t-butyl)—, —PH—, —P(CH$_3$)—, —P(t-butyl)—, —O—, and —S—.

Another metallocene complex developed by the present invention is represented by formula (II), which has a structure similar to formula (I), except that the bonding between M and Y is different and M in formula (II) is a transition metal with an oxidation state of +3.

In formula (II), M can be a Group IIIB transition metal such as scandium and yttrium, a lanthanide, or titanium. The bonding between M and Y is not a covalent bonding, rather, a dative bonding, in which Y donates two electrons to M. The definitions of the rest of the symbols including Z, $R^1$, $R^2$, X, Y and $R^3$ in formula (II) are the same as in formula (I).

For formula (II), representative examples of $Y(R^3)_q$ include OH, OCH$_3$, SH, SCH$_3$, NH$_2$, N(CH$_3$)$_2$, PH$_2$, and P(CH$_3$)$_2$.

In the present invention, the metallocene complex can be combined with an activating coatalyst to form a catalyst composition which can be used for preparing olefin polymers having a high molecular weight.

The activating cocatalyst can be a methyl aluminoxane (MAO), a trialkyl aluminum, a dialkyl aluminum halide, a salt of an inert and non-coordinating anion, or a mixture thereof.

The trialkyl aluminum can be selected from the group consisting of trimethyl aluminum, triethyl aluminum, tripropyl aluminum, trisopropyl aluminum, tributyl aluminum, and triisobutyl aluminum (TIBA).

The inert and non-coordinating anion can be a borate Borates that are suitable for use in the present invention include N,N-dimethyl anilinium tetrakis(pentafluorophenyl) borate, triphenyl carbenium tetrakis(pentafluorophenyl) borate, trimethyl ammonium tetrakis(pentafluorophenyl) borate, ferrocenium tetrakis(pentafluorophenyl)borate, dimethyl ferrocenium tetrakis(pentafluorophenyl)borate, and silver tetrakis(pentafluorophenyl)borate.

Preferably, the activating cocatalyst is methyl aluminoxane, or a mixture of a trialkyl aluminum and a borate.

By using the catalyst composition of the present invention (containing the metallocene complex and the activating cocatalyst), an olefin polymer can be synthesized. In the presence of a catalytically effective amount of the metallocene complex catalyst of the present invention under polymerizing conditions, an olefin can be polymerized (i.e., homopolymerized), or an olefin together with another monomer can be polymerized (i.e., copolymerized).

Suitable olefin monomers can be ethylene or α-olefins. The polymers to be prepared by the process of the present invention can be homopolymers of ethylene, homopolymers of α-olefins, copolymers of α-olefins, and copolymers of ethylene and α-olefins. Examples of the α-olefins include those olefins having 3 to 12 carbon atoms, such as propylene, 1-butene, 1-pentene, 1-hexene, and 1-octene.

More particularly, the catalyst system disclosed in the present invention can be advantageously used to prepare ethylene homopolymers, including high density polyethylene (HDPE) having broad, bimodal, or multimodal, molecular weight distributions for applications such as high molecular weight films and blow molding.

Furthermore, the catalyst system disclosed in the present invention can be advantageously used to prepare a copolymer of ethylene and propylene (EPR). Also, a copolymer of ethylene, a $C_{3-12}$ α-olefin, and a non-conjugated diene can be prepared. More particularly, when the $C_{3-12}$ α-olefin used is propylene, a copolymer of ethylene, propylene, and a non-conjugated diene can be prepared, which is referred to as EPDM. Suitable non-conjugated dienes can be 5-ethylidene-2-norbornene (ENB), 5-methylene-2-norbornene, 5-vinylidene-2-norbornene, 1,4-hexadiene (HD), or dicyclopentadiene (DCPD).

The polymerization can also be carried out in the presence of hydrogen together with the catalyst composition. Thus, the molecular weight of the resulting polymer can be controlled to any desired range.

The catalyst system disclosed in the present invention can be used in slurry reaction conditions, gas phase, and solution polymerization reaction conditions. Polymerization is typically carried out at a temperature of 0° to 250° C., and an atmospheric pressure up to 3,000 psi.

The following examples are intended to illustrate the process and the advantages of the present invention more fully without limiting its scope, since numerous modifications and variations will be apparent to those skilled in the art. Unless otherwise indicated, all parts, percents, ratios and the like are by weight.

Synthesis of Metallocene

EXAMPLE 1

Preparation of $(C_5Me_4H)Li$

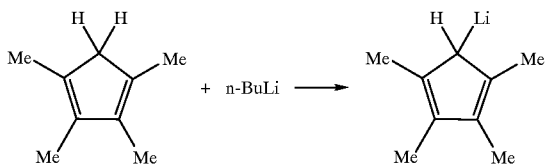

Tetramethylcyclopentadiene (8.57 g, 70.2 mmole) was placed in a 300 ml round bottom flask with 150 ml of diethyl ether. This clear solution was cooled to −78° C. before 1 equivalent of n-butyl lithium (n-BuLi) was injected into it with a syringe. The mixture turned yellow immediately and the color of it faded away gradually. This mixture was allowed to warm to room temperature (about 20–30° C.) and stirred overnight. The mixture was filtered to collect 4.83 g of a lithium salt.

EXAMPLE 2

Preparation of $(C_5Me_4H)(C_3H_6)SiCl$

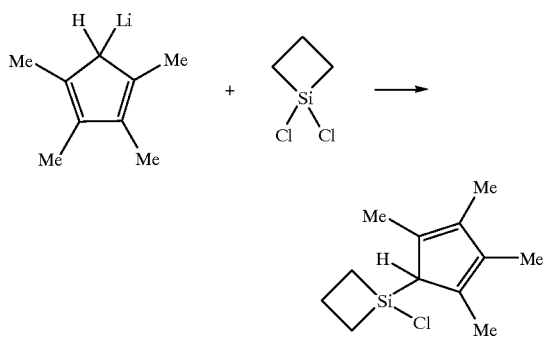

The lithium salt (4.8 g, 0.0375 mole) obtained from Example 1 was suspended in a toluene/THF mixed solvent (2:1 by volume). This slurry was cooled to −78° C. before an excess amount of trimethylenesilyl dichloride was injected into it. The mixture was allowed to warm to room temperature and stirred overnight. Then, the mixture was stripped under vacuum to remove solvent and excess silyl dichloride. Some pentane was added to remove LiCl. The yellow filtrate was stripped again to a light oil (8.05 g).

EXAMPLE 3

Preparation of $(C_5Me_4H)(C_3H_6)Si(t-Bu)NH$

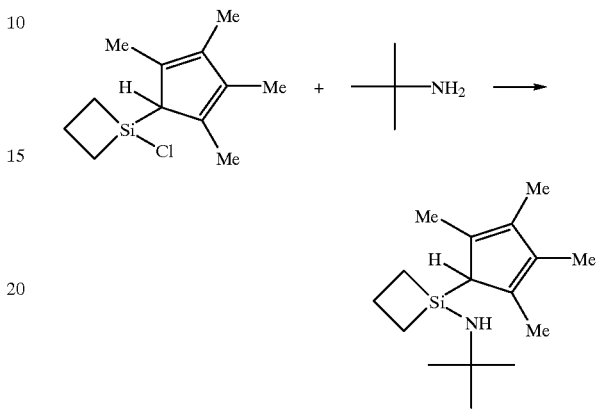

$(C_5Me_4H)(C_3H_6)SiCl$ (8 g, 35.3 mmole) obtained from Example 2 was dissolved in 30 ml of toluene. The solution was cooled to −78° C. before an excess amount of t-butyl amine (2.1 equivalents) was injected into it. The thick slurry was filtered to remove white insolubles. The yellow filtrate was concentrated to obtain 8.10 g of product.

EXAMPLE 4

Preparation of $(C_5Me_4)(C_3H_6)Si(t-Bu)NLi_2$

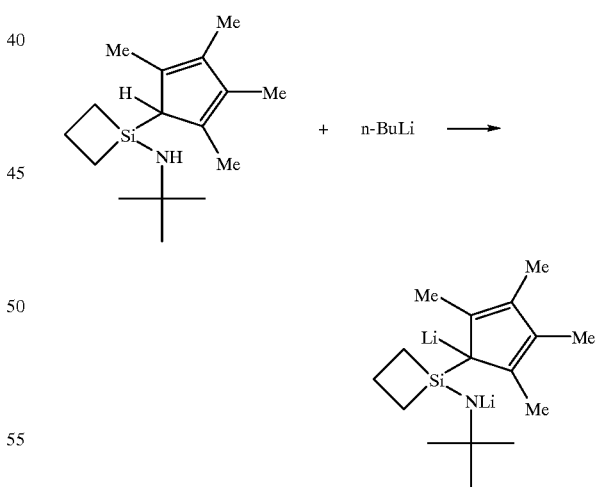

The ligand (8.1 g, 30.78 mmole) obtained from Example 3 was added to 200 ml of diethyl ether. This solution was cooled to −78° C. before 2 equivalents of n-BuLi were injected into it with a syringe. No obvious change was observed. The mixture was stripped to reduce the solvent level to one third of the original amount and the mixture was stirred overnight. It was filtered to collect 7.5 g of a white solid.

EXAMPLE 5

Preparation of $(C_5Me_4)(C_3H_6)Si(t\text{-}BuN)TiCl_2$ [trimethylenesilylcyclopentadienyl-t-butylamido dichloro titanium]

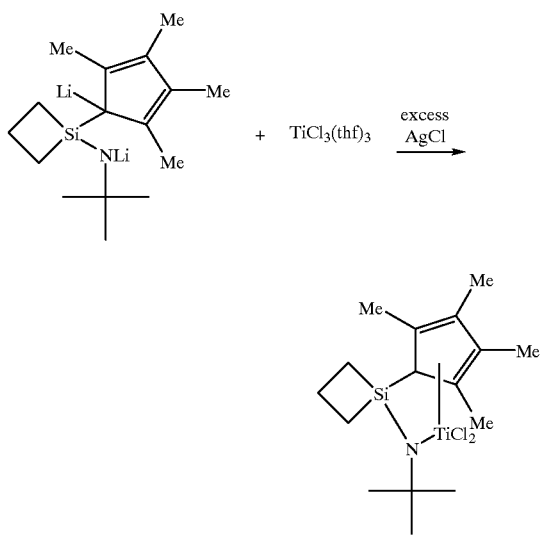

The dilithium salt (2.07 g) obtained from Example 4 and $TiCl_3(thf)_3$, comprising an adduct of tetrahydrofuran with $TiCl_3$, were suspended in 25 ml of THF (tetrahydrofuran) and cooled to −30° C. separately. These two solutions were mixed and stirred. The mixture turned black after 1 hour and turned into a clear solution with a very dark blue color after 3 hours. Then, an excess amount of AgCl (2.1 g) was added to this dark blue solution in a flask wrapped by aluminum foil and stirred overnight in dark.

The reaction mixture was orange-red and clear. The reaction mixture was filtered to remove Ag salts.

The red filtrate was stripped to dryness and the residue was redissolved in 40 ml of toluene. The solution was filtered to remove LiCl, concentrated again to induce a yellow solid to come out, filtered, and collected to give a yellow solid (2.2 g). The yield was about 80%, which was much higher than that of a conventional constrained geometry catalyst (CGC). The $^1H$ NMR spectrum of the solid is shown in FIG. 1.

Figure 2:
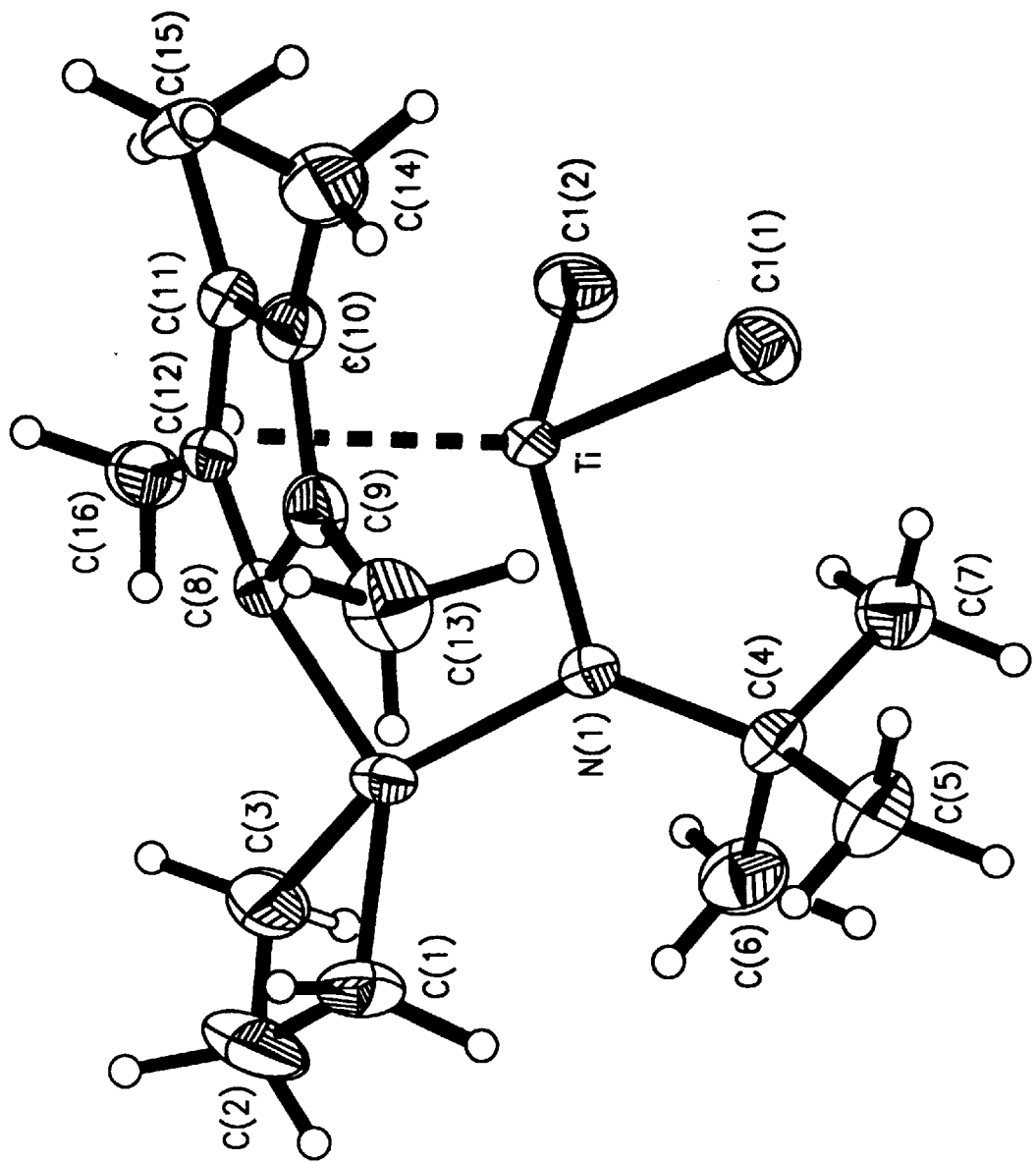
FIG. 2 is a computer generated model of a metallocene product based on single crystal X-ray data.

FIG. 2 is a computer generated model of the metallocene product based on single crystal X-ray data.

EXAMPLE 6

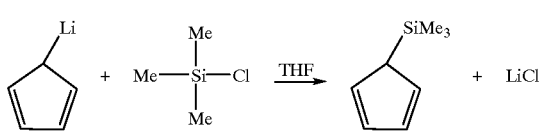

1.9 g of cyclopentadienyl-Li (CpLi) (26.8 mmol) was dissolved in 50 ml of THF, stirred and cooled to −30° C. 3 g of trimethylsilyl chloride (TMSCl) (27.6 mmol) was diluted with 10 ml of THF and this diluted TMSCl was cooled to −30° C. The diluted TMSCl was gradually dropped into the CpLi solution at room temperature and the reaction was allowed to proceed for 24 hours. Then, the mixture was stripped under vacuum to remove solvent. Some pentane was added to remove LiCl. The filtrate was stripped again to afford 2.1 g of $C_5H_5SiMe_3$ as a yellow liquid.

EXAMPLE 7

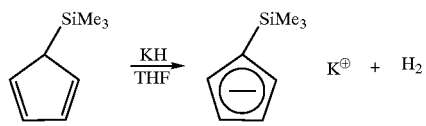

$C_5H_5SiMe_3$(1.9 g) obtained from Example 6 was dissolved in 20 ml of THF. 0.65 g of KH was suspended in 30 ml of THF. These two solution were cooled to −30° C. for more than 30 minutes. The $C_5H_5SiMe_3$ solution was added to the KH solution and the mixture was allowed to warm up to room temperature and stirred overnight. The mixture was filtered to remove excess KH and the filtrate was cooled to −30° C. for use in Example 8.

EXAMPLE 8

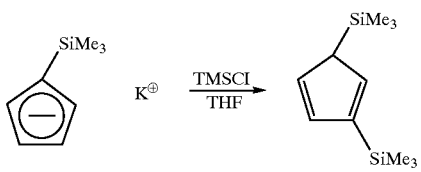

The filtrate of potassium salt obtained from Example 7 was diluted in THF and cooled to −30° C. 1.5 g of TMSCl was diluted with 10 ml of THF and then cooled to −30° C. The TMSCl solution was dropped into the potassium salt solution and the mixture was allowed to warm to room temperature and stirred overnight. Then, the mixture was stripped by vacuum to remove THF. Some pentane was added to remove KCl. The filtrate was stripped again to afford 2.15 g of $C_5H_4(SiMe_3)_2$.

EXAMPLE 9

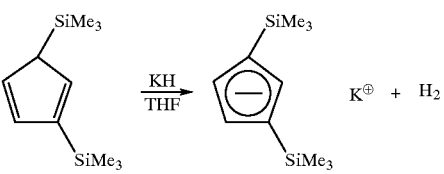

2.15 g of $C_5H_4(SiMe_3)_2$ obtained from Example 8 and 0.42 g of KH were diluted with 30 ml. THF separately and then were cooled to −30° C. The $C_5H_4(SiMe_3)_2$ solution was added dropwise into the KH solution and the mixture was allowed to warm to room temperature and stirred overnight. Then, the mixture was filtered to remove KH. The filtrate was stripped under vacuum to afford 2.457 g of a potassium salt.

EXAMPLE 10

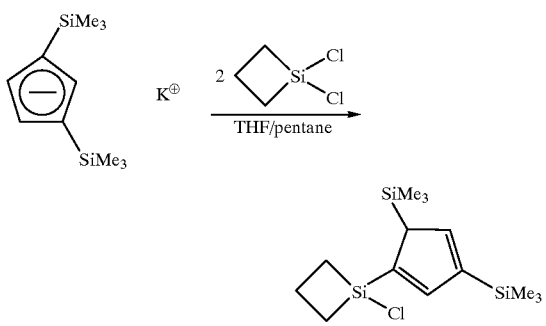

The potassium salt (2.457 g) obtained from Example 9 was dissolved in a 50 ml of THF/pentane mixed solvent (1:1 by volume). This slurry was cooled to −78° C. with liquid nitrogen before an excess amount of trimethylenesilyl dichloride (2.8 g) was injected into it. The mixture was allowed to warm to room temperature and stirred overnight. Then, the reaction mixture was stripped under vacuum to remove the solvent, filtered, and washed with pentane. The filtrate was stripped to a yellow liquid (2.38 g, yield=77%).

EXAMPLE 11

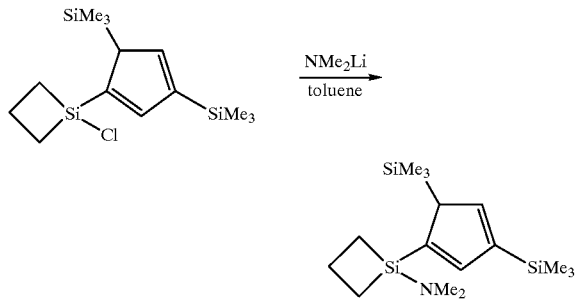

The yellow liquid ($C_5H_3$) $(SiMe_3)_2(C_3H_6)SiCl$ (2.38 g) obtained from Example 10 and $NMe_2Li$ (0.385 g) were dissolved in 20 ml of toluene separately and cooled to −30° C. for about 2 hours. The ($C_5H_3$) $(SiMe_3)_2(C_3H_6)SiCl$ solution was added dropwise to the $Nme_2Li$ solution and the mixture was allowed to warm to room temperature and stirred overnight. The reaction mixture was filtered, stripped under vacuum, and washed with pentane. The filtrate was distilled at 80° C. under vacuum. The 0.74 g of distillate was recovered as a yellow clear liquid (yield=60.5%).

EXAMPLE 12

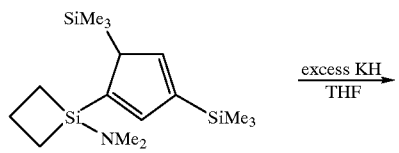

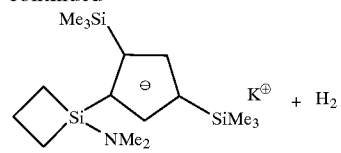

The amine (0.74 g) obtained from Example 11 and KH (0.1 g) were dissolved in 20 ml of THF separately and cooled to −30° C. for 30 minutes. The amine solution was added dropwise to the KH solution and the mixture was allowed to warm to room temperature and stirred overnight. The reaction mixture was filtered, stripped, and washed with pentane. The 0.69 g of distillate was recovered as a pale yellow liquid.

EXAMPLE 13

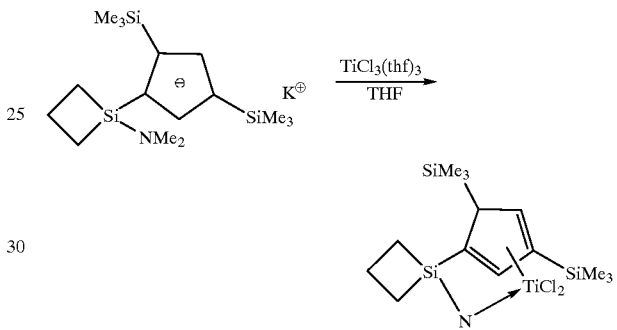

The potassium salt (0.69 g) obtained from Example 12 and $TiCi_3(thf)_3$ (0.707 g) were dissolved in THF separately and cooled to −30° C. The potassium salt solution was added dropwise to the $TiCl_3(thf)_3$ solution and the mixture was allowed to warm to room temperature and stirred for 3 hours. The reaction mixture was stripped, washed with toluene and filtered. The filtrate was stripped to dryness and was recrytallized with toluene/pentane to afford a green solid.

Polymer Synthesis

EXAMPLES 14

Synthesis of ethylene-propylene rubber (EPM)

The reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 80° C., and 500 ml of toluene was charged into the reactor. After the temperature was stabilized, 8 ml ($1.2 \times 10^{-2}$ mole) of MAO was charged into the reactor and stirred. After 5 minutes, 2 ml ($4 \times 10^{-6}$ mole) of the metallocene catalyst obtained from Example 5 in toluene was charged and stirred. After stirring at 80° C. for 1 minute, ethylene and propylene gas (ratio by volume: 40/50) at 100 psi were introduced into the reactor.

After the completion of the polymerization reaction, the solution was cooled and methanol was added to precipitate the product. The product was filtered and dried for various tests. The results obtained are shown in Table 1 below.

EXAMPLES 15 and 16

The same procedures as described in Example 14 were employed, except that the reaction temperature was changed. The results obtained are shown in Table 1.

EXAMPLE 17
Synthesis of ethylene propylene diene rubber (EPDM)

The reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 80° C., and 500 ml of toluene was charged into the reactor. After the temperature stabilized, 8 ml ($1.2 \times 10^{-2}$ mole) of MAO was charged into the reactor and stirred. After 5 minutes, 2 ml ($4 \times 10^{-6}$ mole) of the metallocene catalyst obtained from Example 5 in toluene was charged and stirred. After stirring at 80° C. for 5 minute, 10 ml of 5-ethylidene-2-norbornene (ENB) was charged and stirred. After 1 minute, ethylene and propylene gas (ratio in volume: 40/50) at 100 psi were introduced into the reactor.

After the completion of the polymerization reaction, the solution was cooled and methanol was added to precipitate the product. The product was filtered and dried for various tests. The results obtained are shown in Table 1.

EXAMPLE 18

The same procedures as described in Example 17 were employed, except that the ethylene/propylene feed ratio was changed to 50/40 in volume. The results obtained are shown in Table 1.

Comparative Examples 1–3

The same procedures as described in Example 14 were employed, except that the metallocene catalyst used was replaced by $C_5Me_4(Me_2Si\text{-}N\text{-tert-Bu})TiCl_2$ [dimethylsilyl-cyclopentadienyl-t-butylamidodichloro titanium], which is a constrained geometry catalyst (CGC), the reaction temperature was changed, and the feed ratio of ethylene and propylene gas by volume was changed to 50/50. The results are shown in Table 2 below.

TABLE 2

| Comparative Example | Reaction Temperature (° C.) | Activity ($\times 10^5$ g/g-metal-hr) | Properties of the Products | | | |
|---|---|---|---|---|---|---|
| | | | Tg (° C.) | E/P mole ratio | Mw | MWD |
| 1 | 80 | 1.2 | −43.9 | 63/37 | 334,544 | 2.5 |
| 2 | 100 | 0.51 | −47.3 | 67/33 | 203,518 | 2.36 |
| 3 | 120 | 0.49 | −47.44 | 67/33 | 247,183 | 3.14 |

E/P Feed Ratio = 50/50
Pressure = 100 psi

From the results in Tables 1 and 2 above, it can be seen that the catalyst of the present invention has a higher catalytic activity than that of a conventional CGC. Moreover, the olefin polymer obtained by the catalyst of the present invention has a relatively high molecular weight.

The foregoing description of the preferred embodiments of this invention has been presented for purposes of illustration and description. Obvious modifications or variations are possible in light of the above teaching. The embodiments chosen and described provide an excellent illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 1

| | Reaction Conditions | | | Properties of the Products | | | |
|---|---|---|---|---|---|---|---|
| Example | Temp (° C.) | ENB (ml) | Activity ($\times 10^5$ g/g-metal-hr) | Tg (° C.) | E/P mole ratio | Mw | MWD |
| 14 | 80 | 0 | 3.97 | −39.4 | 43/57 | 368,320 | 3.3 |
| 15 | 95 | 0 | 4.8 | −39 | 41/59 | 157,787 | 2.9 |
| 16 | 110 | 0 | 3.2 | −42.4 | 47/53 | 117,209 | 2.6 |
| 17 | 80 | 10 | 0.8 | −43 | 68/32 | — | — |
| 18 | 80 | 10 | 0.8 | −43 | 68/32 | — | — |

E/P Feed Ratio = 40/50 in Examples 14–17
E/P Feed Ratio = 50/40 in Example 18
Pressure = 100 psi

What is claimed is:

1. A metallocene complex which is represented by the following formula:

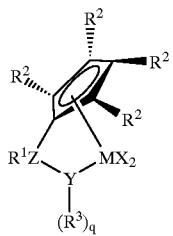

(I)

wherein:

M is a Group IVB transition metal with an oxidation state of +4;

Z is a Group IVA element;

$R^1$ is a divalent unsubstituted or substituted $C_{3-6}$ alkanediyl group which forms a ring system with Z, wherein the substituent is selected from the group consisting of $C_{1-20}$ alkyl, $C_{1-20}$ alkenyl, $C_{6-20}$ aryl, $C_{7-20}$ alkylaryl, and $C_{7-20}$ arylalkyl;

$R^2$ can be the same or different and is H, a $C_{1-20}$ linear, branched or cyclic hydrocarbyl group, or a silyl group, or two adjacent $R^2$ groups combine together to form with the carbon atoms to which they are attached a $C_{4-6}$ fused ring system;

X is independently an anionic ligand with a −1 valence;

Y is a Group VA element or a Group VIA element;

q is 1 when Y is a Group VA element, and q is 0 when Y is a Group VIA element; and $R^3$ is H, or a $C_{1-20}$ linear, branched or cyclic hydrocarbyl group.

2. The metallocene complex as claimed in claim 1, wherein $R^1$ is a divalent unsubstituted $C_{3-6}$ alkanediyl group which forms a ring system with Z.

3. The metallocene complex as claimed in claim 2, wherein $R^1$ is trimethylene.

4. The metallocene complex as claimed in claim 1, wherein Z is Si.

5. The metallocene complex as claimed in claim 1, wherein $R^2$ is independently selected from the group consisting of H, $C_{1-20}$ alkyl, $C_{1-20}$ alkenyl, $C_{6-20}$ aryl, $C_{7-20}$ alkylaryl, $C_{7-20}$ arylalkyl and a silyl group.

6. The metallocene complex as claimed in claim 5, wherein $R^2$ is independently selected from the group consisting of H, methyl, ethyl, propyl, butyl, isobutyl, amyl, isoamyl, hexyl, 2-ethylhexyl, heptyl, octyl, vinyl, allyl, isopropenyl, phenyl, and tolyl.

7. The metallocene complex as claimed in claim 5, wherein $R^2$ is independently selected from the group consisting of methyl silyl, dimethyl silyl, trimethyl silyl, and methyl ethyl silyl.

8. The metallocene complex as claimed in claim 1, wherein two adjacent $R^2$ groups combine together to form with the carbon atoms to which they are attached a $C_{4-6}$ fused ring system.

9. The metallocene complex as claimed in claim 8, wherein $R^2$ groups form with the cyclopentadienyl moiety to which they are attached to give a saturated or unsaturated polycyclic cyclopentadienyl ligand.

10. The metallocene complex as claimed in claim 9, wherein $R^2$ groups form with the cyclopentadienyl moiety to which they are attached to give an indenyl, tetrahydroindenyl, fluorenyl or octahydrofluorenyl group.

11. The metallocene complex as claimed in claim 1, wherein X is selected from the group consisting of H, $C_{1-20}$ hydrocarbyl, halides, alkoxides, aryloxides, and amides.

12. The metallocene complex as claimed in claim 1, wherein q is 1 and Y is a Group VA element.

13. The metallocene complex as claimed in claim 1, wherein q is 0 and Y is a Group VIA element.

14. The metallocene complex as claimed in claim 1, wherein $R^3$ is selected from the group consisting of H, $C_{1-20}$ alkyl, $C_{1-20}$ alkenyl, $C_{6-20}$ aryl, $C_{7-20}$ alkylaryl, and $C_{7-20}$ arylalkyl.

15. A metallocene complex catalyst composition for producing an olefin polymer, comprising:

(a) the metallocene complex as claimed in claim 1; and (b) an activating cocatalyst selected from the group consisting of methyl aluminoxane, a trialkyl aluminum, a dialkyl aluminum halide, a salt of an inert and non-coordinating anion, and mixtures thereof.

16. The catalyst composition as claimed in claim 15, wherein the trialkyl aluminum is selected from the group consisting of trimethyl aluminum, triethyl aluminum, tripropyl aluminum, trisopropyl aluminum, tributyl aluminum, and triisobutyl aluminum.

17. The catalyst composition as claimed in claim 15, wherein the inert and non-coordinating anion is a borate.

18. The catalyst composition as claimed in claim 17, wherein the borate is selected from the group consisting of N,N-dimethyl anilinium tetrakis(pentafluorophenyl)borate, triphenyl carbenium tetrakis(pentafluorophenyl)borate, trimethyl ammonium tetrakis(pentafluorophenyl)borate, ferrocenium tetrakis(pentafluorophenyl)borate, dimethyl ferrocenium tetrakis(pentafluorophenyl)borate, and silver tetrakis (pentafluorophenyl)borate.

19. The catalyst composition as claimed in claim 15, wherein the activating cocatalyst is methyl aluminoxane.

20. The catalyst composition as claimed in claim 15, wherein the activating cocatalyst is a mixture of a trialkyl aluminum and a borate.

21. A process for preparing an olefin polymer, comprising the step of (1) polymerizing an olefin, or (2) polymerizing an olefin with another monomer, under polymerizing conditions in the presence of a catalytically effective amount of the metallocene complex catalyst composition comprising:

(a) a metallocene complex which is represented by the following formula:

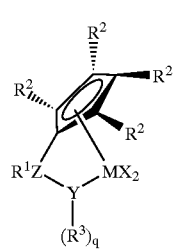

(I)

wherein:

M is a Group IVB transition metal with an oxidation state of +4;

Z is a Group IVA element;

$R^1$ is a divalent unsubstituted or substituted $C_{3-6}$ alkanediyl group which forms a ring system with Z, wherein the substituent is selected from the group consisting of $C_{1-20}$ alkyl, $C_{1-20}$ alkenyl, $C_{6-20}$ aryl, $C_{7-20}$ alkylaryl, and $C_{7-20}$ arylalkyl;

$R^2$ can be the same or different and is H, a $C_{1-20}$ linear, branched or cyclic hydrocarbyl group, or a silyl group, or two adjacent $R^2$ groups combine together to form with the carbon atoms to which they are attached a $C_{4-6}$ fused ring system;

X is independently an anionic ligand with a −1 valence;

Y is a Group VA element or a Group VIA element;

q is 1 when Y is a Group VA, element, and q is 0 when Y is a Group VIA element; and $R^3$ is H, or a $C_{1-20}$ linear, branched or cyclic hydrocarbyl group; and (b) an activating cocatalyst selected from the group consisting of methyl aluminoxane, a trialkyl aluminum, a dialkyl aluminum halide, a salt of an inert and non-coordinating anion, and mixtures thereof.

22. The process as claimed in claim 21, wherein the process comprises polymerizing an olefin and the olefin is ethylene.

23. The process as claimed in claim 21, wherein the process comprises polymerizing at least one olefin with another monomer, and wherein the olefin is ethylene and the other monomer is at least one α-olefin having 3 to 12 carbon atoms.

24. The process as claimed in claim 23, wherein the process comprises polymerizing at least one olefin with at least another monomer, and wherein the olefin is ethylene and the other monomer is propylene.

25. The process as claimed in claim 21, wherein the process comprises polymerizing an olefin and the olefin is an α-olefin having 3 to 12 carbon atoms.

26. The process as claimed in claim 21, wherein the process comprises polymerizing an olefin with another monomer, and wherein both the olefin and the other monomer are selected from the group consisting of α-olefins having 3 to 12 carbon atoms.

27. The process as claimed in claim 21, wherein the process comprises polymerizing at least one olefin with another monomer, and wherein the olefin includes ethylene and a $C_{3-12}$ α-olefin and the other monomer is a non-conjugated diene.

28. The process as claimed in claim 27, wherein the non-conjugated diene is selected from the group consisting of 5-ethylidene-2-norbornene, 5-methylene-2-norbornene, 5-vinylidene-2-norbornene, 1,4-hexadiene, and dicyclopentadiene.

29. The process as claimed in claim 21, wherein the polymerization is conducted in the presence of hydrogen.

30. A metallocene complex which is represented by the following formula:

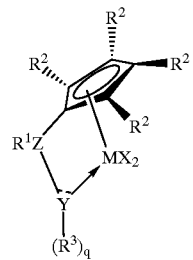

(II)

wherein:

M is selected from the group consisting of a Group IIIB transition metal, a lanthanide, and Ti with an oxidation state of +3;

Z is a Group IVA element;

$R^1$ is a divalent unsubstituted or substituted $C_{3-6}$ alkanediyl group which forms a ring system with Z, wherein the substituent is selected from the group consisting of $C_{1-20}$ alkyl, $C_{1-20}$ alkenyl, $C_{6-20}$ aryl, $C_{7-20}$ alkylaryl, and $C_{7-20}$ arylalkyl;

$R^2$ can be the same or different and is H, a $C_{1-20}$ linear, branched or cyclic hydrocarbyl group, or a silyl group, or two adjacent $R^2$ groups combine to form with the carbon atoms to which they are attached a $C_{4-6}$ fused ring system;

X is independently an anionic ligand with a −1 valence;

Y is a Group VA element or a Group VIA element;

q is 2 when Y is a Group VA element, and q is 1 when Y is a Group VIA element; and $R^3$ is H, or a $C_{1-20}$ linear, branched or cyclic hydrocarbyl group.

31. The metallocene complex as claimed in claim 30, wherein $R^1$ is a divalent unsubstituted $C_{3-6}$ alkanediyl group which forms a ring system with Z.

32. The metallocene complex as claimed in claim 31, wherein $R^1$ is trimethylene.

33. The metallocene complex as claimed in claim 30, wherein Z is Si.

34. The metallocene complex as claimed in claim 30, wherein $R^2$ is independently selected from the group consisting of H, $C_{1-20}$ alkyl, $C_{1-20}$ alkenyl, $C_{6-20}$ aryl, $C_{7-20}$ alkylaryl, and $C_{1-20}$ arylalkyl, and a silyl group.

35. The metallocene complex as claimed in claim 34, wherein $R^2$ is independently selected from the group consisting of H, methyl, ethyl, propyl, butyl, isobutyl, amyl, isoamyl, hexyl, 2-ethylhexyl, heptyl, octyl, vinyl, allyl, isopropenyl, phenyl, and tolyl.

36. The metallocene complex as claimed in claim 34, wherein $R^2$ is independently selected from the group consisting of methyl silyl, dimethyl silyl, trimethyl silyl, and methyl ethyl silyl.

37. The metallocene complex as claimed in claim 30, wherein two adjacent $R^2$ groups combine to form with the carbon atoms to which they are attached a $C_{4-6}$ fused ring system.

38. The metallocene complex as claimed in claim 37, wherein $R^2$ groups form with the cyclopentadienyl moiety to which they are attached to give a saturated or unsaturated polycyclic cyclopentadienyl ligand.

39. The metallocene complex as claimed in claim 38, wherein $R^2$ groups form with the cyclopentadienyl moiety to which they are attached to give an indenyl, tetrahydroindenyl, fluorenyl or octahydrofluorenyl group.

40. The metallocene complex as claimed in claim 30, wherein X is selected from the group consisting of H, $C_{1-20}$ hydrocarbyl, a halide, an alkoxide, an aryloxide, and an amide.

41. The metallocene complex as claimed in claim 30, wherein q is 2 and Y is a Group VA element.

42. The metallocene complex as claimed in claim 30, wherein q is 1 and Y is a Group VIA element.

43. The metallocene complex as claimed in claim 30, wherein $R^3$ is selected from the group consisting of H, $C_{1-20}$ alkyl, $C_{1-20}$ alkenyl, $C_{6-20}$ aryl, $C_{7-20}$ alkylaryl, and $C_{7-20}$ arylalkyl.

44. A metallocene complex catalyst composition for producing an olefin polymer, comprising:
(a) the metallocene complex as claimed in claim 30; and
(b) an activating cocatalyst selected from the group consisting of methyl aluminoxane, a trialkyl aluminum, a dialkyl aluminum halide, a salt of an inert and non-coordinating anion, and mixtures thereof.

45. The catalyst composition as claimed in claim 44, wherein the trialkyl aluminum is selected from the group consisting of trimethyl aluminum, triethyl aluminum, tripropyl aluminum, trisopropyl aluminum, tributyl aluminum, and triisobutyl aluminum.

46. The catalyst composition as claimed in claim 44, wherein the inert and non-coordinating anion is a borate.

47. The catalyst composition as claimed in claim 46, wherein the borate is selected from the group consisting of N,N-dimethyl anilinium tetrakis(pentafluorophenyl)borate, triphenyl carbenium tetrakis(pentafluorophenyl)borate, trimethyl ammonium tetrakis(pentafluorophenyl)borate, ferrocenium tetrakis(pentafluorophenyl)borate, dimethyl ferrocenium tetrakis(pentafluorophenyl)borate, and silver tetrakis (pentafluorophenyl)borate.

48. The catalyst composition as claimed in claim 44, wherein the activating cocatalyst is methyl aluminoxane.

49. The catalyst composition as claimed in claim 44, wherein the activating cocatalyst is a mixture of a trialkyl aluminum and a borate.

50. A process for preparing an olefin polymer comprising the step of
(1) polymerizing an olefin, or
(2) polymerizing an olefin with another monomer, under polymerizing conditions in the presence of a catalytically effective amount of the metallocene complex catalyst composition comprising:
(a) a metatocene complex which is represented by the following formula:

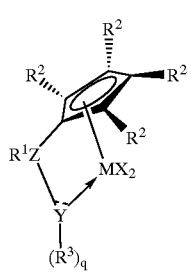

(II)

wherein:

M is selected from the group consisting of a Group IIIB transition metal, a lanthanide, and Ti with an oxidation state of +3;

Z is a Group IVA element;

$R^1$ is a divalent unsubstituted or substituted $C_{3-6}$ alkanediyl group which forms a ring system with Z, wherein the substituent is selected from the group consisting of $C_{1-20}$ alkyl, $C_{1-20}$ alkenyl, $C_{6-20}$ aryl, $C_{7-20}$ alkylaryl, and $C_{7-20}$ arylalkyl;

$R^2$ can be the same or different and is H, a $C_{1-20}$ linear, branched or cyclic hydrocarbyl group, or a silyl group, or two adjacent $R^2$ groups combine to form with the carbon atoms to which they are attached a $C_{4-6}$ fused ring system;

X is independently an anionic ligand with a −1 valence;

Y is a Group VA element or a Group VIA element;

q is 2 when Y is a Group VA element and q is 1 when Y is a Group VLA element; and $R^3$ is H, or a $C_{1-20}$ linear, branched or cyclic hydrocarbyl group and;

(b) an activating cocatalyst selected from the group consisting of methyl aluminoxane, a trialkyl aluminum, a dialkyl aluminum halide, a salt of an inert and non-coordinating anion, and mixtures thereof.

51. The process as claimed in claim 50, wherein the process comprises polymerizing an olefin and the olefin is ethylene.

52. The process as claimed in claim 50, wherein the process comprises polymerizing at least one olefin with another monomer, and wherein the olefin is ethylene and the other monomer is at least one α-olefin having 3 to 12 carbon atoms.

53. The process as claimed in claim 52, wherein the process comprises polymerizing at least one olefin with at least another monomer, and wherein the olefin is ethylene and the other monomer is propylene.

54. The process as claimed in claim 50, wherein the process comprises polymerizing an olefin and the olefin is an α-olefin having 3 to 12 carbon atoms.

55. The process as claimed in claim 50, wherein the process comprises polymerizing an olefin with another monomer, and wherein both the olefin and the other monomer are an α-olefin having 3 to 12 carbon atoms.

56. The process as claimed in claim 50, wherein the process comprises polymerizing an at least one olefin with another monomer, and wherein the olefin includes ethylene and a $C_{3-12}$ α-olefin and the other monomer is a non-conjugated diene.

57. The process as claimed in claim 56, wherein the non-conjugated diene is selected from the group consisting of 5-ethylidene-2-norbornene, 5-methylene-2-norbornene, 5-vinylidene-2-norbornene, 1,4-hexadiene, and dicyclopentadiene.

58. The process as claimed in claim 50, wherein the polymerization is conducted in the presence of hydrogen.

* * * * *